United States Patent
Berger et al.

Patent Number: 5,679,798
Date of Patent: Oct. 21, 1997

[54] SILICONE MONOMERS HAVING A CARBOXYL FUNCTIONAL GROUP THEREON

[75] Inventors: Abe Berger, Summit; Dennis L. Fost, Ringwood, both of N.J.

[73] Assignee: Mona Industries, Inc., Paterson, N.J.

[21] Appl. No.: 754,974

[22] Filed: Nov. 22, 1996

[51] Int. Cl.$^6$ .................. C07F 7/02; C07F 7/10
[52] U.S. Cl. ........................................ 548/406
[58] Field of Search ............................. 548/406

[56] References Cited

U.S. PATENT DOCUMENTS

| | | | |
|---|---|---|---|
| 4,173,569 | 11/1979 | Banfi et al. | 548/406 X |
| 4,476,308 | 10/1984 | Aschwanden et al. | 548/406 X |
| 4,939,126 | 7/1990 | Kurono et al. | 548/406 X |
| 5,596,061 | 1/1997 | Berger et al. | 548/406 |

*Primary Examiner*—Paul F. Shaver
*Attorney, Agent, or Firm*—Franklyn Schoenberg; Norman E. Lehrer

[57] ABSTRACT

There is provided organosilane compounds containing one or more carboxyl acid group(s) that may be represented by the general formula:

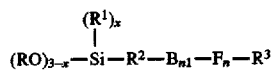

wherein:

R which can be the same or different, are hydrogen, and monovalent hydrocarbon radicals and substituted hydrocarbon radicals $R^1$ which can be the same or different can be substituted or unsubstituted alkyl, substituted or unsubstituted aryl, alkenyl, alkynyl or $-R^2-B_{n1}-F_n-R^3$;

x can be zero to 3;

$R^2$ is linear or branched alkylene of 1–12 carbon atoms, preferably propylene or isobutylene;

B is $-NR^6$, sulfur or oxygen;

$R^6$ is hydrogen or lower alkyl ($C_{1-6}$);

$n^1$ is zero or 1;

F is linear or branched alkylene of 1–10 carbon atoms, preferably ethylene;

n is zero or 1, with the proviso that if $n^1$ is 1, n is 1 and if $n^1$ is 0, n is 0;

$R^3$ is

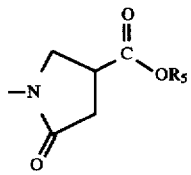

$R^5$ is hydrogen, lower alkyl ($C_{1-6}$) or alkali metal.

11 Claims, No Drawings

SILICONE MONOMERS HAVING A CARBOXYL FUNCTIONAL GROUP THEREON

FIELD OF THE INVENTION

The present invention relates to organosilane compounds and, more particularly to novel organosilane compounds containing a carboxyl acid group and/or its derviratives to a method of making the same.

BACKGROUND OF THE INVENTION

Various organosilane monomers or compounds containing one or more functional groups such as amines, vinyls, mercaptans, epoxies, halogens, and the like are widely known. These compounds have been used in a variety of ways such as coupling agents and adhesion promoters for inorganic materials, as reactants for modifying the properties of organic polymers, as crosslinking agents for curable organic polymers systems, as additives for a variety of home care and personal care compositions, as well as monomers for the preparation of silicon containing polymers.

While silane monomers or compounds containing amine and diamine functional groups are well known and can be readily prepared, silane monomers containing carboxyl acid or functional carboxyl groups including an amphoteric class of organosilanes are generally not known or available commercially. Heretofore, no convenient method for directly preparing silane monomers with free carboxyl acid functional groups has been known or suggested and indirect procedures would generally have to be used for their preparation. Accordingly, the development of silane monomers or compounds containing one or more functional carboxyl groups and a method for readily preparing such compounds would be desirable and it would be particularly advantageous if such method employed readily available materials such as amino-functional silanes, not only for preparing the novel carboxyl-functional organosilane monomers including an amphoteric class of such compounds and the salts or esters thereof, but a variety of organosilane and organosilicone derivatives thereof as well.

While, as indicated, organosilane monomers or compounds containing a variety of functional groups and methods for preparing the same have, heretofore, been known and used, there is no known disclosure or suggestion of the novel carboxyl-functional organosilane compounds of the present invention or of the method for making the same herein described.

SUMMARY OF THE INVENTION

It is accordingly an object of the present invention to provide a novel class of organosilane compounds having at least one carboxyl acid functional group thereon.

It is another object of the present invention to provide a novel class of organosilane compounds having a novel type of pyrrolidone containing carboxyl-functional group thereon.

It is a further object of the present invention to provide a novel class of amphoteric organosilane compounds.

It is yet another object of the present invention to provide a process for readily producing organosilane compounds containing at least one carboxyl-functional group including an amphoteric class of organosilane compounds.

In accordance with the present invention, there has now been discovered novel organosilane compounds containing one or more carboxyl acid group(s) and/or the ester or salt derivatives thereof that may be represented by the following general formula:

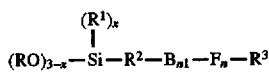

wherein:

R which can be the same or different, are hydrogen,and monovalent hydrocarbon radicals and substituted hydrocarbon radicals such as alkyl and alkoxyalkyl radicals; aryl radicals (phenyl or substituted phenyl); aralkyl radicals; alkenyl or alkynyl radicals; and cycloalkyl radicals;

$R^1$ which can be the same or different can be substituted or unsubstituted alkyl, substituted or unsubstituted aryl, alkenyl, alkynyl or $-R^2-B_{n1}$, $-F_n$ $-R^3$;

x can be zero to 3;

$R^2$ is linear or branched alkylene of 1–12 carbon atoms, preferably propylene or isobutylene;

B is $-NR^6$, sulfur or oxygen;

$R^6$ is hydrogen or lower alkyl ($C_{1-6}$);

$n^1$ is zero or 1;

F is linear or branched alkylene of 1–10 carbon atoms, preferably ethylene;

n is zero or 1, with the proviso that if $n^1$ is 1, n is 1 and if $n^1$ is 0, n is 0;

$R^3$ is

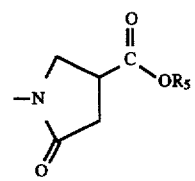

$R^5$ is hydrogen, lower alkyl ($C_{1-6}$) or alkali metal.

In another aspect of the present invention there is provided a method for preparing organosilane monomers containing one or more pyrrolidone-containing functional carboxylic acid groups and/or the ester or salt thereof, which comprises reacting an amine- or diamine-functional organosilane monomer having at least one primary amine group with itaconic acid or an ester thereof at an elevated temperature (preferably from about 90° C. to about 130° C.) for a time sufficient to react, preferably substantially completely react (generally ranging from 1–5 hours), the itaconic acid or ester thereof with the primary amine group(s) on the silane monomer to form an organosilane monomer having at least one pyrrolidone-containing carboxyl functional group.

DESCRIPTION OF THE PREFERRED EMBODIMENTS

In accordance with the present invention there are provided novel organosilane monomers or compounds containing one or more, preferably one, carboxyl functional group (s), including an amphoteric class of organosiliane monomers, and/or the esters or salts thereof, which may be represented by the general formula:

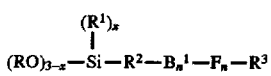

wherein:
- R which can be the same or different, are selected from hydrogen, and monovalent hydrocarbon radicals and substituted hydrocarbon radicals such as alkyl radicals, preferably lower alkyl ($C_1$–$C_6$); alkoxyalkyl radicals; aryl radicals, preferably phenyl or substituted phenyl; aralkyl radicals, e.g. benzyl, phenylethyl etc.; alkenyl radicals, e.g. vinyl, allyl, cyclohexenyl, etc. radicals; alkynyl radicals; and cycloalkyl radicals, e.g. cycloheptyl, etc. radicals;
- $R^1$ which can be the same or different, can be substituted or unsubstituted alkyl, preferably lower alkyl ($C_{1-6}$); substituted or unsubstituted aryl; alkenyl; alkynyl or —$R^2$—$B_n^1$—$F_n$—$R^3$;
- x can be zero to 3;
- $R^2$ is linear or branched alkylene of 1–12 carbon atoms, preferably propylene and isobutylene;
- B is —$NR^6$, sulfur or oxygen;
- $R^6$ is H or lower alkyl ($C_{1-6}$);
- $n^1$ is zero or 1;
- F is linear or branched alkylene of 1–10 carbon atoms, preferably ethylene;
- n is zero or 1, with the proviso that if $n^1$ is 1, n is 1 and if $n^1$ is 0, n is 0;
- $R^3$ is

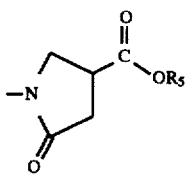

$R_5$ is H, lower alkyl ($C_{1-6}$) or alkali metal.

The novel carboxyl-functional organosilane monomers of the present invention including an amphoteric class of organosilane monomers, surprisingly and unexpectedly can be readily and directly prepared by the reaction of an amino-functional organosilane monomer having one or more functional primary amine group(s) or functional diamine group(s) wherein at least one of the amino groups is a primary amine group, with up to about one equivalent, preferably about stoichiometric quantities, of itaconic acid or its ester per primary amine group at an elevated temperature for a time sufficient for substantially all of the itaconic acid or its ester to react with the primary amine group(s) and the formation of pyrrolidone-containing carboxyl-functional group(s) therefrom.

In general, from about 0.5, preferably from about 0.9 to about 1.1, equivalents of itaconic acid or its ester per functional primary amine group is reacted with the primary amine group(s) of the amine or diamine functional organosilane monomer wherein substantially all the itaconic acid, and preferably all the primary amine group(s) are reacted and an organsilane compound with at least one pyrrolidone-containing functional carboxyl acid group(s) and/or its ester or salt is formed.

The reaction can be carried out neat or in an inert solvent such as alcohol, hydrocarbon solvent, chlorinated hydrocarbon and the like, as desired, in general, at elevated temperatures up to about 175° C., preferably from about 90° C. to about 130° C. The reaction readily proceeds and generally complete reaction of the itaconic acid or its ester with the available primary amine group(s) occurs in the Michael Addition Reaction manner with the double bond of the itaconic acid followed by immediate cyclization to form a pyrrolidone group, which will occur in from about 1 to 5 hours. Routine analytical techniques for amine and acid values as well as monitoring viscosity, color and water and/or alcohol evolution can be used to determine completion of the reaction.

Amine-functional organosilane monomers suitable for use in accordance with the practice of the invention are compounds that may be represented by the formula:

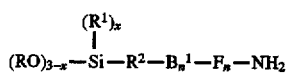

wherein:
- R which can be the same or different, can be selected from hydrogen; and monovalent hydrocarbon and monovalent substituted hydrocarbon radicals such as alkyl radicals, preferably lower alkyl ($C_{1-6}$); alkoxyalkyl radicals; aryl radicals, preferably phenyl or substituted phenyl; aralkyl radicals, e.g. benzyl, phenylethyl, etc.; alkenyl radicals, e.g. vinyl, allyl, cyclohexenyl etc. radicals; alkynyl radicals; and cycloalkyl, e.g. cycloheptyl, etc; with the proviso that the various R substituents are compatible with each other and the $NH_2$ group;
- $R^1$, which can be the same or different can be substituted or unsubstituted alkyl, preferably lower alkyl ($C_{1-6}$); substituted or unsubstituted aryl; alkenyl; alkynyl; or —$R^2$—$B_n^1$—$F_n$—$NH_2$;
- x can be zero to 3;
- $R^2$ is linear or branched alkylene of 1–12 carbon atoms, preferably propylene and isobutylene;
- B is —$NR^6$, sulfur or oxygen;
- $R^6$ is H or lower alkyl ($C_{1-6}$); $n^1$ is zero or 1;
- F is linear or branched alkylene of 1–10 carbon atoms, preferably ethylene;
- n is zero or 1 with the proviso that if $n^1$ is 1, n is 1 and if $n^1$ is 0, n is 0.

Suitable amine-functional organosilane monomers include organosilane compounds having one or more primary amine functional group(s) and organosilane compounds having one or more functional diamine group(s) wherein at least one of the amino groups is a primary amine group. While, as indicated, anine-functional organosilane compounds suitable for use in accordance with the practice of the invention may also include a variety of other substituent groups, it would be evident to those having skill in the art that compounds having substituent groups which are not compatible with other substituent groups and/or with the primary amine grops, such as halogen, isocyanato and acyloky groups would not be suitable for use. Suitable compounds are well known and are available commercially, for example, from Dow Corning, General Electric, Th. Goldschmidt AG, Shin-Etsu; OSi division of Witco and H üls.

Exemplary suitable amine functional silane monomers include aminopropyl trimethoxysilane, aminopropyl triethoxysilane, aminoisobutyl triethoxy or trimethoxysilane, aminoethylthiopropyl triethoxysilane, aminopropylmethyl diethoxy or dimethoxy silane aminopropoxypropyl trimethoxy silane, aminoundecyl trimethoxy silane, aminopropyl phenyldimethoxy silane, aminopropyl dimethylmethoxy silane and aminobutyl methyl dimethoxy silane. Exemplary suitable functional diamine silane monomers, preferably for use in the preparation of an amphoteric class of silane monomers, include organosilanes having one or more functional aminoalkylaminoalkylene groups such as aminoethylaminopropyl trimethoxy or triethoxy silane, aminoethylaminoisobutyl triethoxy or trimethoxy silane and aminoethylaminoisobutylmethyl diethoxy or dimethoxy silane.

As indicated, the pyrrolidone-containing carboxyl-functional organosilane monomers or compounds of the present invention including the amphoteric class of organosilane monomers of the present invention are readily prepared by reaction of amine-functional organosilane monomers as herein described with itaconic acid or its ester. Itaconic acid (methylene succinic acid) is a compound of the formula:

wherein $R^6$, which can be the same or different, is hydrogen or lower alkyl (1–6 carbon atoms).

The compound itaconic acid is available commercially from Pfizer Chemicals Division and Rhone Poulenc whereas ester derivatives thereof are available from Morflex, Inc., Greensboro, N.C. The compounds are produced by known fermentation techniques although chemical synthesis methods are also known.

The organosilane monomers according to the present invention are useful, for example, as coupling agents and adhesion promoters for inorganic materials, as reactants for modifying the properties of organic polymers, as crosslinking agents for curable organic polymers, as additives for personal and home care products, as precursors for a wide variety of organo- and organosilicone polymers of varying molecular weights and the like.

The above is a general description of the present invention. The following examples are given for the purpose of illustration and are not intended in any way to limit the invention as claimed. Unless noted to the contrary, proportions are on a weight basis.

EXAMPLE 1

This experiment illustrates the method for making N-(Trimethoxysllylpropyl)-4-carboxy pyrrolidone A mixture of 22.1 grams of gamma aminopropyl trimethoxy-silane (0.1 mole) and 13 grams of itaconic acid is formed in a reaction vessel. A heterogeneous mixture initially results. The mixture is slowly heated to about 110° –115° C. with agitation whereupon a slightly exothermic reaction occurs and a clear melt results with some water being evolved. The product is examined by IR and its structure is consistent with N-Trimethoxysilylpropyl)-4-carboxyl pyrrolidone.

EXAMPLE 2

A reaction mixture of 41.2 grams 3-(Aminoethyl) aminopropylmethyldimethoxysilane and 31.6 grams of dimethyl itaconate is charge to a reaction vessel with good agitation and heated carefully to about 120° C. A mild exothurm occurs resulting in a clear melt with the simultaneous evolution of methanol. The reaction mixture is heated at 120° C. for 3 hours. An alkali number determination at this point indicates that the primary amino group is preferentially reacted (alkali number of 160 vs. theoretical of 162). Analysis by NMR confirms the structure of the product to be methyl N-(methyldimethoxysilyl pyrrolidone ethyl pyrrolidone-4-methylcarboxylate.

EXAMPLE 3

This experiment illustrates the synthesis of N-(Trimethoxysilylpropylaminoethyl-4-carbomethoxy pyrrolidone.

A mixture of 44.5 grams of aminoethylaminopropyl trimethoxysilane (0.2 mole) and 31.6 grams of dimethyl itaconate are charged to a reaction vessel and slowly heated with agitation to about 130° C. An exothermic reaction occurs, methanol is distilled from the system and a clear melt liquid results. The reaction mixture is heated at 125° C. for 3 hours. The alkali number of the reaction product is 150 compared to a required number of 161.

EXAMPLE 4

This experiment illustrates the preparation of N-(mixed hydroxy, ethoxysilylpropyl)-4-carboxy pyrrolidone.

A mixture of 44.2 grams (0.2 mole) of aminopropyl triethoxysilane obtained as KB903 from Shin Etsu with 26 grams of itaconic acid which forms a solid dispersed in a liquid is charged to a reaction vessel. The mixture is slowly heated with agitation to 90° C. whereupon an exotherm results which raises the reaction mixture temperatures to 125° C. At 125° C., a clear yellow homogenous melt results with water and ethanol being formed. The alkali number of the product is zero and an acid number of 195° C. The product is very soluble in water

EXAMPLE 5

This example illustrates the preparation of N-(Diethoxymethylsilyl propyl)-4-Carbomethoxy pyrrolidone.

A mixture of 38.2 grams aminopropylmethyldiethoxy silane (0.2 moles) and 31.6 grams of dimethyl itaconate are charged to a reaction vessel with agitation. A slight exotherm occurs raising the reaction mixture temperature from about 26° C. to about 46° C. The reaction is allowed to proceed at 82° C. for 6 hours after which the reaction mixture is distilled at 153° –155° C., 6 mm. with the collection of 112 grams of a colorless liquid. The alkali number of the reaction product is zero.

EXAMPLE 6

This example illustrates the preparation of N-(Trimethoxysilyl propoxypropyl)-4-carbomethoxy pyrrolidone.

A reaction mixture of 30.2 grams of aminopropoxypropyl trimethoxy silane (0.2 mole) ad 38.2 grams of dimethyl itaconate is charged to a reaction vessel with agitation which results in a slight exotherm. The reaction mixture is heated for 6 hours at 110° C. and then distilled at reduced pressure. A colorless liquid reaction product is isolated and the structure is confirmed by NMR and IR.

EXAMPLE 7

This example illustrates the preparation of N-(Triethoxysilylpropylthiopropyl)-4-carboethoxy pyrrolidone.

A reaction mixture of 0.2 moles of aminopropylthio propyltriethoxysilane and equivalent weight of ethyl itaconate is charged to a reaction vessel with agitation and heated at about 95° C. for 6 hours. After distillation under reduced pressure a colorless liquid reaction product is isolated.

EXAMPLE 8

This example illustrates the preparation of 1,1,1,3,5,5,5-heptamethyl-3-[4-carboxyl pyrrolidone-1-yl-propyl] trisiloxane.

Equal molar proportions of 1,1,1,3,5,5,5 heptamethyl-3-aminopropyl trisiloxane and itaconic acid are charged to a reaction vessel and heated, with agitation, for 6 hours at 110°–120° C. The reaction mixture is isolated as a colorless liquid having an alkali number of zero.

What is claimed is:

1. Organosilane compounds containing one or more carboxyl acid group(s), and the ester or the salt derivatives thereof that may be represented by the following general formula:

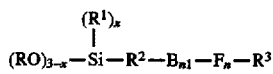

wherein:
- R which can be the same or different, are selected from hydrogen, monovalent hydrocarbon radicals or substituted hydrocarbon radicals;
- $R^1$ which can be the same or different, are selected from substituted or unsubstituted alkyl, substituted or unsubstituted aryl, alkenyl, alkynyl or $—R^2—B_{n1}—F_n—R^3$;
- x can be zero to 3;
- $R^2$ is linear or branched alkylene of 1–12 carbon atoms.
- B is $—NR^6$, sulfur or oxygen;
- $R^6$ is hydrogen or lower alkyl ($C_{1-6}$);
- $n^1$ is zero or 1;
- F is linear or branched alkylene of 1–10 carbon atoms; n is zero or 1, with the proviso that if $n^1$ is 1, n is 1 and if $n^1$ is 0, n is 0;
- $R^3$ is

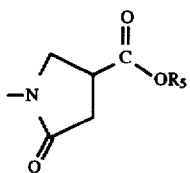

$R^5$ is hydrogen, lower alkyl ($C_{1-6}$) or alkali metal.

2. The organosilane compounds as claimed in claim 1, wherein R are selected from hydrogen; alkyl radicals; alkoxyalkyl radicals; aryl radicals; aralkyl radicals; alkenyl radicals; alkynyl radicals; cycloalkyl radicals or mixtures of the same.

3. The organosilane compounds as claimed in claim 1, wherein $R^1$ is selected from substituted or unsubstituted lower alkyl ($C_{1-6}$); substituted or unsubstituted aryl; alkenyl; alkynyl or mixture of the same.

4. The organosilane compounds as claimed in claim 1, wherein said compounds are an amphoteric class of silane compounds, B is $—NR^6$ and $R^1$ is selected from substituted or unsubstituted alkyl; substituted or unsubstituted aryl; alkenyl; or alkynyl.

5. The method of preparing carboxyl-functional organosilane monomers, which comprises reacting an amino-functional organosilane monomer having one or more functional primary amine group(s) or functional diamine group(s) wherein at least one of the amino groups is a primary amine group, with up to about one equivalent of itaconic acid or its ester per primary amine group at an elevated temperature for a time sufficient for substantially all of the itaconic acid or its ester to react with the primary amine group(s) and the formation of pyrrolidone-containing carboxyl-functional group(s) therefrom.

6. The method of preparing carboxyl-functional organosilane monomers as claimed in claim 5, wherein said amino-functional organosilane monomer having a functional primary amine group is reacted with about a stoicheometric amount of itaconic acid or its ester per primary amine group.

7. The method of preparing carboxyl-functional organosilane monomers as claimed in claim 5, wherein said amine-functional organosilane monomer has a functional diamine group wherein one of the amine groups is a primary amine groups which is reacted with about a stoichiometric amount of itaconic acid or its ester per primary amine group and said carboxyl functional organosilane monomers prepared thereby is an amphoteric class of silane monomers.

8. The method of preparing carboxyl-functional organosilane monomers as claimed in claim 5, wherein said amino-functional organosilane monomer reactant is aminopropyl-triethoxy silane.

9. The method of preparing carboxyl-functional organosilane monomers as claimed in claim 5, wherein said amino-functional organosilane monomer reactant is aminopropyl-trimethoxy silane.

10. The method of preparing carboxyl-functional organosilane monomers as claimed in claim 5, wherein said amino-functional organosilane monomer reactant is aminopropylmethyldiethoxy silane.

11. The method of preparing carboxyl-functional organosilane monomers as claimed in claim 5, wherein said amino-functional organosilane monomer reactant is aminopropylmethy dimethyoxy silane.

* * * * *